(12) United States Patent
Gilman

(10) Patent No.: US 9,770,548 B2
(45) Date of Patent: Sep. 26, 2017

(54) TRANSANAL IRRIGATION KIT

(71) Applicant: Hollister Incorporated, Libertyville, IL (US)

(72) Inventor: Thomas H. Gilman, Spring Grove, IL (US)

(73) Assignee: Hollister Incorporated, Libertyville, IL (US)

( * ) Notice: Subject to any disclaimer, the term of this patent is extended or adjusted under 35 U.S.C. 154(b) by 435 days.

(21) Appl. No.: 14/354,027

(22) PCT Filed: Oct. 11, 2012

(86) PCT No.: PCT/US2012/059759
§ 371 (c)(1),
(2) Date: Apr. 24, 2014

(87) PCT Pub. No.: WO2013/070377
PCT Pub. Date: May 16, 2013

(65) Prior Publication Data
US 2014/0276631 A1    Sep. 18, 2014

Related U.S. Application Data

(60) Provisional application No. 61/557,141, filed on Nov. 8, 2011.

(51) Int. Cl.
*A61M 3/02*    (2006.01)

(52) U.S. Cl.
CPC ........ *A61M 3/0262* (2013.01); *A61M 3/0279* (2013.01); *A61M 2210/1064* (2013.01); *A61M 2210/1067* (2013.01)

(58) Field of Classification Search
CPC .............. A61M 3/0262; A61M 3/0279; A61M 2210/1067; A61M 2210/1064; A61M 25/0041; A61M 25/0068; A61M 2025/0073; A61M 2025/0024
See application file for complete search history.

(56) References Cited

U.S. PATENT DOCUMENTS

| 1,720,198 | A | 7/1929 | Ballreich |
| 1,847,954 | A | 3/1932 | Fisher |
| 2,442,573 | A | 6/1948 | Stafford |
| 3,344,791 | A | 10/1967 | Foderick |

(Continued)

FOREIGN PATENT DOCUMENTS

| WO | WO 98/23312 | 6/1998 |
| WO | WO 01/49345 | 7/2001 |
| WO | WO 2011/023196 | 3/2011 |

OTHER PUBLICATIONS

International Preliminary Report of Patentability for PCT/US2012/059759 dated May 13, 2014.

(Continued)

*Primary Examiner* — Nathan R Price
*Assistant Examiner* — Melissa A Snyder
(74) *Attorney, Agent, or Firm* — Cook Alex Ltd.

(57) ABSTRACT

An anal irrigation kit provides an improved approach for emptying a bowel by instilling irrigation liquid and stimulating the rectal wall simultaneously. The anal irrigation kit includes an irrigation liquid reservoir, a hand pump, and a soft flow manifold, which can be folded for insertion into a rectum.

16 Claims, 2 Drawing Sheets

(56) References Cited

U.S. PATENT DOCUMENTS

| | | | |
|---|---|---|---|
| 3,916,896 A | 11/1975 | Ballard | |
| 4,321,920 A | 3/1982 | Gillig | |
| 4,637,814 A * | 1/1987 | Leiboff | A61M 1/0084 |
| | | | 604/27 |
| 4,682,979 A | 7/1987 | Girouard | |
| 5,074,842 A | 12/1991 | Clayton | |
| 5,871,463 A | 2/1999 | Baker et al. | |
| 6,722,782 B2 | 4/2004 | Faries, Jr. et al. | |
| 7,530,976 B2 | 5/2009 | MacMahon et al. | |
| 8,777,912 B2 * | 7/2014 | Nishtala | A61M 3/0283 |
| | | | 604/327 |
| 2003/0036682 A1 | 2/2003 | Leber et al. | |
| 2003/0073974 A1 | 4/2003 | Falconer | |
| 2003/0074018 A1 | 4/2003 | Torstensen et al. | |
| 2004/0267198 A1 | 12/2004 | Torstensen et al. | |
| 2006/0009732 A1 * | 1/2006 | Hardy | A61M 3/0262 |
| | | | 604/35 |
| 2008/0058650 A1 * | 3/2008 | Saadat | A61M 25/1002 |
| | | | 600/478 |
| 2009/0312696 A1 * | 12/2009 | Copa | A61M 25/007 |
| | | | 604/43 |
| 2010/0191183 A1 * | 7/2010 | Tanghoej | A61M 25/0017 |
| | | | 604/96.01 |
| 2010/0191194 A1 | 7/2010 | Tanghoej | |
| 2010/0210901 A1 | 8/2010 | Makower et al. | |
| 2010/0280489 A1 | 11/2010 | Nishtala et al. | |
| 2010/0292644 A1 | 11/2010 | Haack et al. | |
| 2012/0150046 A1 * | 6/2012 | Watson | A61B 5/0071 |
| | | | 600/478 |

OTHER PUBLICATIONS

European Patent Office, Partial Supplementary European Search Report, counterpart EP Appl. No. 12847602, dated Jun. 17, 2015.

* cited by examiner

TRANSANAL IRRIGATION KIT

CROSS-REFERENCE TO RELATED APPLICATIONS

This is a National Stage Application of International Patent Application No. PCT/US2012/059759, filed Oct. 11, 2012, which claims the benefit of and priority to U.S. Provisional Application No. 61/557,141, filed Nov. 8, 2011, the contents of which are incorporated fully by reference herein.

BACKGROUND

The present disclosure relates to bowel irrigation devices, more particularly to a transanal irrigation kit for instilling irrigation fluid into the rectal cavity while also simultaneously stimulating the reflex defecatory response.

Anal irrigation kits and methods to stimulate the rectal reflex reaction are well known for use by individuals afflicted with neurogenic bowel dysfunction. Neurogenic bowel dysfunction is a disruption of the normal function of the bowel commonly associated with persons suffering from spinal cord injuries, amyotrophic lateral sclerosis, spina bifida, multiple sclerosis, and diabetes mellitus.

In the most common form of this dysfunction, the bowel will respond reflexively to certain stimuli, but the person cannot empty the bowel with cognitive volition. One method for emptying the bowel for these patients is the general approach referred to as bowel irrigation. In this approach a fairly large amount of liquid is instilled into the bowel, filling the lower bowel. Traditionally this is done by a gravity feed of the liquid, which is a relatively slow liquid instillation. This results in the emptying of the bowel. It is, however, not known to what extent the reflex bowel reaction is involved in bowel emptying as a result of the irrigation. It is thought that this irrigation technique works by mobilizing the bowel contents in the liquid.

This technique typically requires more than 500 mL and up to 2000 mL of liquid and usually takes a considerable amount of time, up to 30 minutes. The fluid path into the rectum is typically provided by a flow manifold having a cone-shaped end, which flares toward the distal direction, such that the narrow end of the cone is inserted into the rectum. The reverse flared end keeps the user from inserting the rigid tubing end too far into the rectum. The cone-shaped end of the flow manifold is typically fairly rigid to facilitate insertion, and so its use presents at least some risk of anal and rectal trauma.

Many of these irrigation systems require the user to hold the flow manifold in place during instillation of the liquid. To improve upon the inconvenience of having to hold the manifold in place during the irrigation process, some irrigation systems including a retention cuff or a balloon to retain the flow manifold in the rectum have been developed. However, the retention cuff or balloon can be overinflated, and increase the risk of rectal trauma. Further, there have been reports of the balloons rupturing due to over inflation, resulting in an alarming noise and destruction of the product. Furthermore, the retention cuff or the balloon inflation step takes time, and often adds complexity to the irrigation systems.

Another disadvantage of current bowel irrigation kits is their size. They are generally large, unwieldy, and take up a lot of storage space. This makes them inconvenient for travel and indiscreet in the home. An important factor in their large size is that the liquid reservoir in these current bowel irrigation kits is designed to hold two liters or more in irrigation liquid. This in turn requires the reservoir to be able to rest on the floor, or to be hung in a location remote from the point of use, which in rum requires a fairly long tubing set to conduct the liquid from the reservoir to the point of use.

Another general and commonly used approach for emptying the bowel is digital stimulation. This approach involves inserting a finger or a dilstick into the rectum, pressing on the rectal wall with the finger or the dilstick, and rotating the finger or the dilstick in a circular manner to stimulate the bowel reflex. This stimulation of the rectal wall causes a reflex reaction that is a defecatory response of the lower bowel. The reflex reaction includes the initiation of peristaltic waves beginning at the splenic flexure, which is the start of the descending colon, down through the sigmoid, and into the rectum. This response also includes relaxation of the internal anal sphincter, which enables emptying of the lower bowel.

The details of digital stimulation required for a robust reflex response are known only through the trial and error of experience. It seems that multiple stimulation episodes and rotation of the finger around the rectal wall are both important for a good bowel response. The digital stimulation does not require liquid instillation, thus results in less bowel output to manage, and bowel evacuation can proceed somewhat faster than gravity fed irrigation. However, digital stimulation does require inserting a finger or a dilstick into the rectum, which can present a significant risk of trauma for the anal canal and for the rectum.

Accordingly, there is a need for an improved transanal irrigation kit that provides a lower risk of trauma and a more efficient bowel emptying process, which can be easily manipulated by the user.

BRIEF SUMMARY

A transanal irrigation kit, which provides both irrigation fluid instillation into the rectum, and safe and reliable stimulation of the rectal wall for initiation of the bowel reflex defecatory response, is provided according to various embodiments of the present disclosure. The transanal irrigation kit provides for an improved bowel emptying approach that has a low risk of trauma by use of a soft flow manifold. The soft flow manifold includes a flare at the proximal end and multiple fluid openings for directing fluid streams toward multiple different areas along the rectal wall. The flow manifold is configured such that the flared-end portion can be folded and inserted past the anal canal and into the rectum. Once in the rectum, the flared-end portion self deploys and serves to maintain the flow manifold in place during instillation of the irrigation fluid, without the need to hold the manifold in place by hand. This hands free system for holding the manifold in place eliminates the need for a retention balloon or a cuff that requires inflation.

Further, the irrigation system provides rectal wall stimulation with controlled pressure fluid streams. This significantly reduces the risk of trauma when compared to use of a finger or a dilstick. A further advantage is that effective bowel emptying can be achieved with significantly smaller fluid instillation volumes.

In one aspect, an anal irrigation kit includes an irrigation liquid reservoir, a pump, which is in fluid communication with the irrigation liquid reservoir, and a flow manifold, which is in fluid communication with the pump. The flow manifold includes multiple openings and configured to be folded by a user for insertion into a rectum. The flow manifold is made of a soft, resilient polymeric material, such that the flow manifold is sufficiently stiff to be pushed through an anal canal and self-deployable once in the rectum, but soft enough to be manually foldable for insertion into the rectum. In one embodiment, the flow manifold is made of a silicone rubber. Further, the flow manifold includes a flared-end portion, which includes a flared wall and a cover portion. A flow lumen is defined between the manifold walls and cover portion. A distal end of the flared end portion is closed by the cover portion having a circular profile, the circular profile having a diameter between about 1.5 cm and about 7 cm.

The multiple openings are arranged on the cover portion, and the anal irrigation kit is configured to direct liquid streams in different directions through the multiple openings at a pressure sufficient to stimulate a rectal wall. The multiple openings are configured such that at least one of the multiple openings directs the liquid stream toward the rectal wall at a pressure sufficient to trigger a reflex reaction. In one embodiment, the multiple openings include a center opening arranged proximate a center of the cover portion and at least three peripheral openings arranged along a periphery of the cover portion, wherein each of the peripheral openings directs a fluid stream toward a different location along a polar coordinate. In some embodiments, the pump is a hand pump, and the anal irrigation kit is configured to control a pressure of a fluid stream output through each of the multiple openings by adjusting a volume of fluid expelled by the hand pump per squeeze and a size of each of the multiple openings and a number of multiple openings. In other embodiments pumping devices other than hand operated pumping devices may be utilized. Some embodiments may have the liquid reservoir entirely integrated with the liquid chamber within the pumping device.

In another aspect, an anal irrigation kit includes an irrigation liquid reservoir, which has an inlet, a first wall and a second wall. The first wall and the second wall are sealed together along peripheral edges to define a cavity. The anal irrigation kit also includes a hand pump, which includes a rigid outer wall, a top inlet and a bottom outlet. The liquid reservoir and the hand pump are connected by tubing. In one embodiment, the liquid reservoir is sized to hold less than 500 cc of liquid, and the tubing connecting the reservoir to the hand pump is less than 20 cm in length. In some embodiments, the irrigation liquid reservoir includes a hole, a circumference of which is of a distance to accommodate a user's thumb.

Further, the anal irrigation kit includes a flow manifold, which has a flow lumen therethrough. The flow manifold has an entry end proximate the hand pump and an exit end, which has a flared-end portion. The flared-end portion has an outer surface area and an inner surface area, and at least two openings. The anal irrigation kit is configured such that a flow of an irrigation fluid is channeled through the flow lumen and the multiple openings at a stimulatory pressure. Further, the flow of the irrigation fluid through the flow manifold urges the outer surface area of the flared cover to engage an inner wall of a rectal cavity. The hand pump and the flow manifold are connected via a series of tubing portions. In one embodiment, at least one of the multiple openings is circumferentially located about a distal end of the flared-end portion. Further, the hand pump has a first one-way valve located proximate the top inlet and a second one-way valve located proximate the bottom outlet. In some embodiments, the irrigation liquid reservoir includes a hole, a circumference of which is of a distance to accommodate a user's thumb. In another embodiment, the anal irrigation kit includes a temperature indicator arranged on a wall of the irrigation liquid reservoir.

In yet another aspect, a handheld transanal irrigation kit, which has a proximal end and a distal end, includes an irrigation liquid reservoir, a hand pump, and a resilient flow manifold. The irrigation liquid reservoir includes an inlet, and a first wall and a second wall, which are sealed together along peripheral edges to define a cavity. The hand pump includes a rigid outer wall, a top inlet and a bottom outlet, and has a first one-way valve located proximate the top inlet and a second one-way valve located proximate the bottom outlet. The flow manifold is constructed of a soft, resilient material, and has a flow lumen therethrough. The manifold has an entry end proximate the hand pump and an exit end, which includes a flared cover. The flared cover has an outer surface area and an inner surface area, and includes at least two openings. The transanal irrigation kit is configured such that a flow of an irrigation fluid is channeled through the flow lumen and the openings and exits the openings at a stimulatory pressure.

In another aspect, a method of emptying a bowel includes the step of providing an anal irrigation kit, which includes an irrigation liquid reservoir, a hand pump, and a soft flow manifold including multiple openings. Further, the method includes the steps of folding the soft flow manifold and inserting the folded soft flow manifold into a rectum, and instilling an irrigation liquid and stimulating a rectal wall simultaneously by operation of the hand pump. The soft flow manifold is formed of a soft resilient material, and configured to self-deploy once the folded soft flow manifold is in the rectum. Further, the soft flow manifold includes a flared-end portion, which is folded to increase a bending stiffness of the flared-end portion for insertion into the rectum, which self-deploys in the rectum without a user intervention to provide for hands-free retention of the flow manifold in the rectum during the step of instilling irrigation liquid. The step of instilling an irrigation liquid and stimulating a rectal wall includes expelling liquid streams through the multiple openings, such that at least some of the liquid streams are directed to different areas of the rectal wall at a stimulatory pressure to trigger a defecatory response. The method empties the bowel by mobilizing bowel contents in the irrigation liquid and simultaneously stimulating a defecatory response by expelling irrigation liquid streams at multiple locations along the rectal wall at a stimulatory pressure.

Other aspects, objectives and advantages will become more apparent from the following detailed description when taken in conjunction with the accompanying drawings.

BRIEF DESCRIPTION OF THE SEVERAL VIEWS OF THE DRAWINGS

The benefits and advantages of the present embodiments will become more readily apparent to those of ordinary skill in the relevant art after reviewing the following detailed description and accompanying drawings, wherein.

DETAILED DESCRIPTION

While the present device is susceptible of embodiment in various forms, there is shown in the figures and will hereinafter be described a presently preferred embodiment with the understanding that the present disclosure is to be considered an exemplification of the device and is not intended to be limited to the specific embodiment illustrated.

Figure 1:
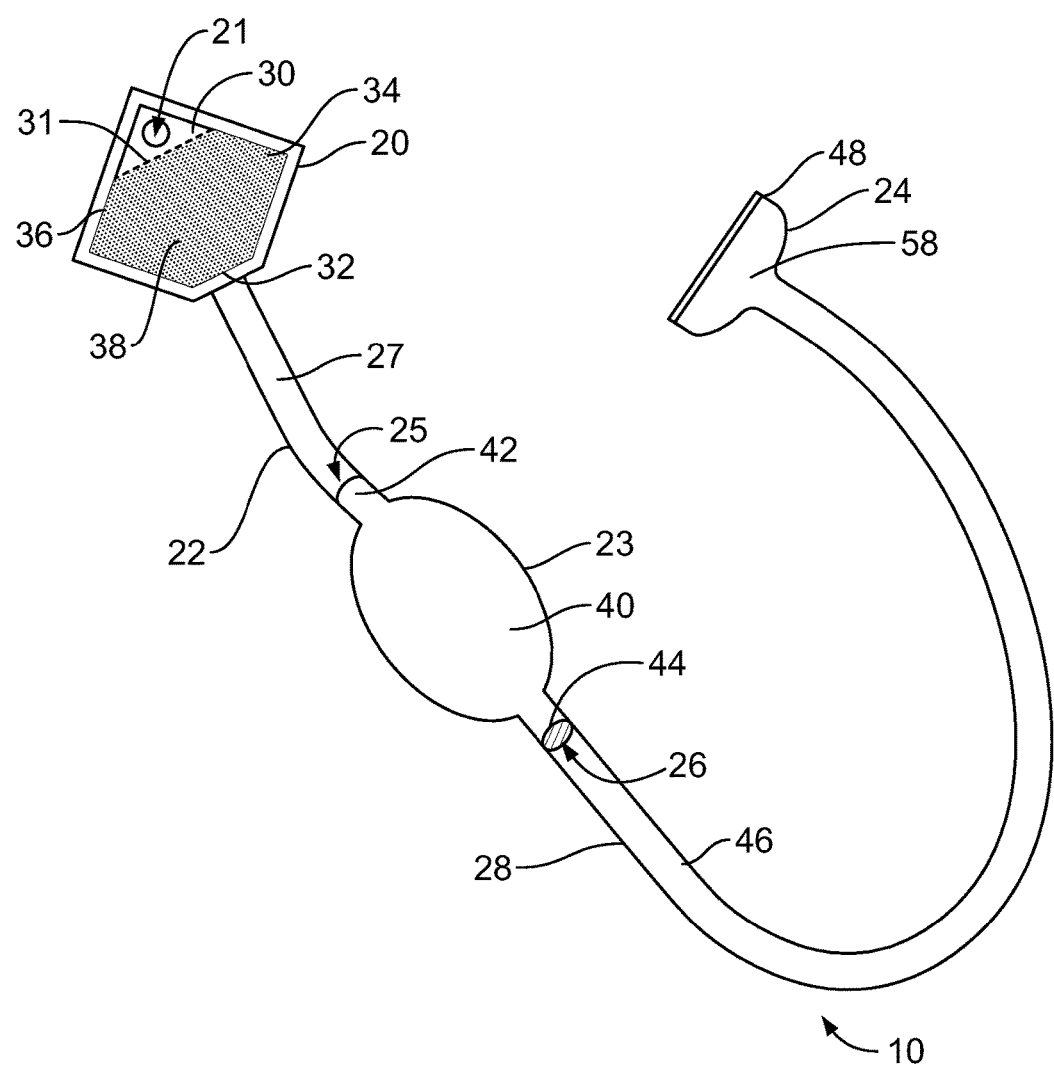
FIG. 1 is a perspective view of an embodiment of a transanal irrigation kit including an irrigation fluid reservoir, a hand pump, and a flow manifold according to an embodiment.

Referring to the figures, FIG. 1 shows an embodiment of a transanal irrigation kit 10. The irrigation kit 10 generally includes an irrigation fluid reservoir 20, a hand pump 23, a flow manifold 24 including multiple fluid openings 52 (FIGS. 2 and 3), and tubing potions 22, 28. The transanal irrigation kit 10 is configured for handheld use by deploying the soft now manifold 24 within the rectal cavity and activating the flow of liquid into the rectum by squeezing the hand pump 23.

The irrigation fluid reservoir 20 includes an inlet 30, an outlet 32, and walls 34, which are sealed together along peripheral edges 36 to define a cavity 38. The walls 34 are formed of a suitable polymeric material, preferably a thin, flexible polymeric film, which is heat sealable. The reservoir 20 has an opening 21 through the reservoir walls that allows suspension of the reservoir 20, for example, from a user's thumb. The reservoir 20 includes the inlet 30, through which the cavity 38 can be filled with liquid. The inlet 30 includes a liquid tight closure 31, preferably, a resealable closure. In one embodiment, the closure 31 is provided in a form of an interlocking closure device, such as a plastic zipper. The reservoir 20 can include a temperature indicator to indicate the temperature of the liquid in the reservoir 20. The reservoir 20 can be provided in different volumes or sizes. Preferably, the reservoir 20 is a small volume reservoir, for example, no more than 500 mL in capacity.

As shown in FIG. 1, the irrigation fluid reservoir 20 is attached to the hand pump 23 via tubing portion 22. Preferably, the tubing portion is no longer than 20 cm, more preferably no longer than 10 cm, most preferably no longer than 3 cm. The hand pump 23 generally includes a pump body 40, an inlet 42, and an outlet 44. One end of the tubing portion 22 is attached to the irrigation fluid reservoir 20 at the outlet 32, and the other end of the tubing portion 22 is attached to the hand pump 23 at the inlet 42, thereby providing a fluid path 27 from the reservoir 20 to the hand pump 23. An advantageous embodiment would have no tubing portion 22, but rather the outlet 32 of the fluid reservoir communicates directly with the inlet 42 of the hand pump. Tubing portion 28 is attached at the outlet 44 of the hand pump 23, providing a fluid path 46 from the pump body 40 to the flow manifold 24. In one embodiment, tubing 28 and flow manifold 24 are continuously formed as a single piece member. Alternatively, the tubing portion 28 and the flow manifold 24 are provided as two separate members sealingly attached to each other. A preferred embodiment is where the two separate members 28 and 24 are attached in a releasable way, to allow for disposal and replacement of the flow manifold with reuse of the remainder of the kit.

Further, the irrigation kit 10 includes one way valves 25, 26, e.g. check valves, that allow fluid to exit the pump body 40 through the outlet 44 when the pump body 40 is squeezed and prevents backflow to the reservoir 20, and to enter through the inlet 42 when the pump body 40 is allowed to relax and prevent draining liquid from the manifold 20. Upon exiting, the hand pump 23, the fluid travels through the tubing portion 28 and into a flow lumen 58 of the flow manifold 24. In other embodiments, the irrigation kit 10 can have other liquid pumping devices alternative to a hand pump to transport the irrigation liquid from the irrigation fluid reservoir 20 and force the liquid out through the multiple openings 52. Some embodiments may also lack a separate liquid reservoir, instead having the liquid reservoir entirely integrated with the liquid chamber that is within the pumping device.

Figure 2:
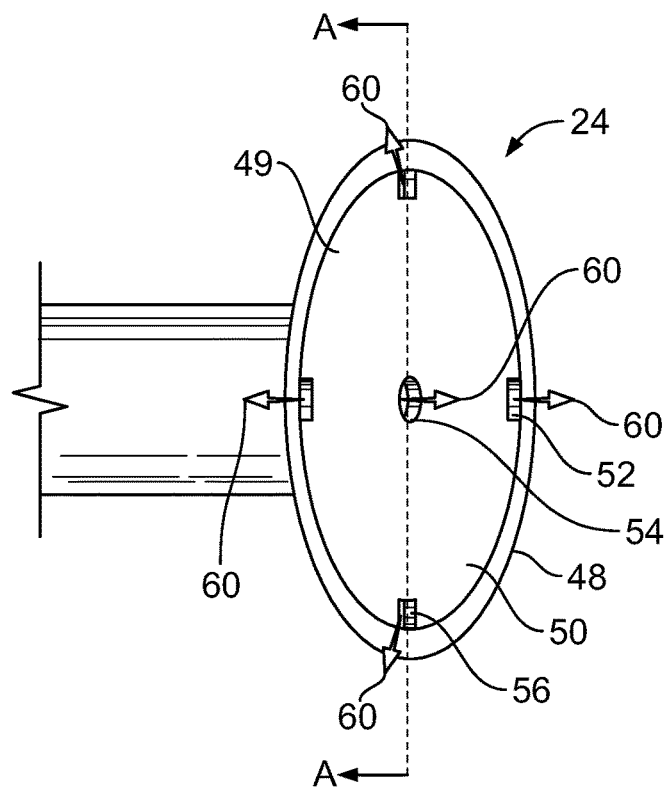
FIG. 2 is a perspective enlarged view of the flow manifold according an embodiment.
Figure 3:
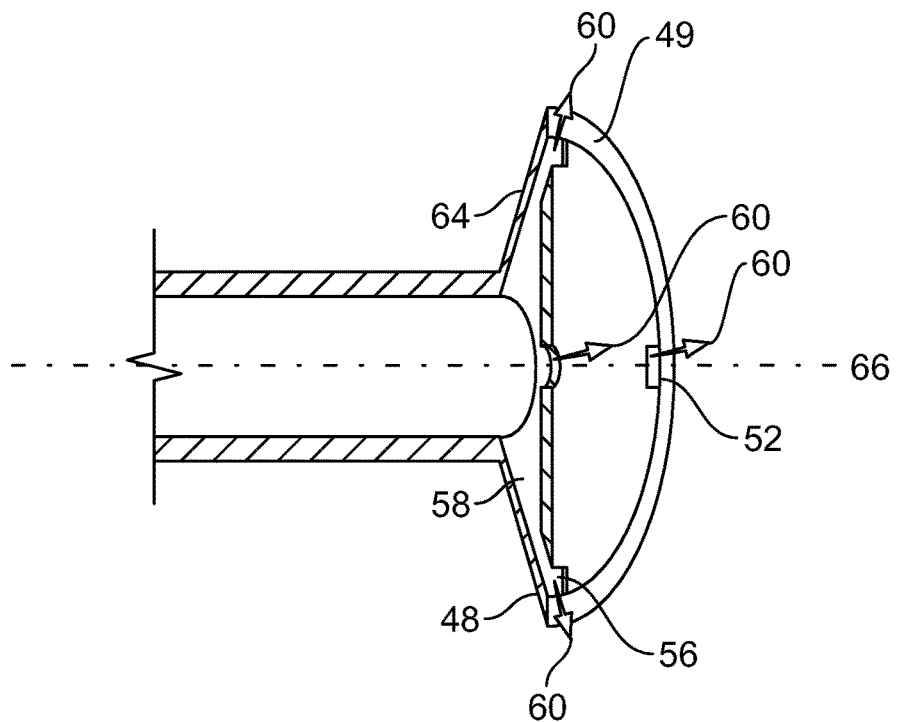
FIG. 3 is a cross sectional view of the flow manifold of FIG. 2.

The flow manifold 24 is located at the proximate end of the irrigation kit 10. FIGS. 2 and 3 show the flow manifold 24 including a flared-end portion 48, the flow lumen 58 (FIG. 3), and multiple fluid openings 52. In this embodiment, the flow lumen 58, which is in fluid communication with the tubing portion 28 has a circular cross-section, a diameter of which increases toward a distal end 49 of the flared-end portion 48. The distal end 49 of the flared-end portion 48 is closed with a cover portion 50, and includes the multiple fluid openings 52.

The distal end 49, including the cover portion 50, has a circular profile or shape, which has a diameter between about 1.5 cm and about 7 cm, preferably between about 5 cm and about 2.5 cm, and more preferably between about 2.5 cm and about 3.5 cm. Further, the flow manifold 24 has a wall 64 having a thickness between about 0.3 mm and about 3.0 mm, preferably between about 0.5 mm and about 2 mm, and more preferably between about 0.7 mm and about 1.5 mm. The flow lumen 58 in the flared-end portion 48 is defined between the wall 64 and the cover portion 50. Although, the flow manifold 24 distal end 49 has a circular shape, in other embodiments, the flow manifold can have a non-circular shaped distal end, such as a distal end having an oval profile or shape.

The flow manifold 24 is made of a soft, flexible, or pliable material, such that it can be folded and inserted past the anal canal and into the rectum. Further, the flared-end portion 48 is configured such that once it is in the rectum, the flared-end portion 48 self-deploys due to the resiliency of the material. When the flared-end portion 48 deploys in the rectum, it serves to maintain the flow manifold 24 in place during instillation of the irrigation fluid by operation of the hand pump 23. Further, as irrigation fluid streams are expelled out of the flow manifold 24 through the multiple openings 52 at a sufficient pressure to stimulate the rectal walls via the hand pump 23, the negative force of the fluid stream output forces the outer surface area of the deployed flared-end portion 48 to engage an inner wall of the rectal cavity to provide a temporary seal between the anal canal and the rectum, thereby reducing the risk of leakage during instillation of the irrigation fluid.

Suitable materials for the flow manifold 24 include flexible or pliable polymeric materials, which have sufficient resiliency to provide the self-deploying capability of the flared-end portion 48, for example, certain polyurethane rubbers or latex rubbers, and preferably, silicone rubbers. A flow manifold 24 made of such soft and rubbery polymeric materials substantially reduces the risk of rectal trauma when compared to rather rigid flow manifolds of conventional irrigation systems and a finger or a dilstick for digital stimulation. Further, when folded, the flow manifold 24 provides sufficient stiffness to be pushed through the anal canal, yet is still soft enough to prevent trauma to the anal canal, and to be manually foldable for insertion into the rectum. As stiffness is typically a function of a thickness, the user can simply double fold the flow manifold, which makes it four times thicker than the wall thickness of the flow manifold. This in turn increases the bending stiffness by about 16 times to provide sufficient stiffness for a user to manually insert the flow manifold 24 past the anal canal. Once the flow manifold 24 deploys in the rectum, the rectal walls only encounter the soft flared-end portion 48 with a single wall thickness, which poses a significantly lower possibility of causing trauma to the rectal walls. In other embodiments, the flow manifold 24 can be folded or gathered in various different was to provide for sufficient functional bending stiffness for insertion into the rectum.

The distal end 49 of the flow manifold 24, including the cover portion 50, includes multiple fluid openings 52, which allow the irrigation fluid to be forced out of the flow lumen 58 by operation of the hand pump 23. In this embodiment, the flow manifold 24 includes five openings 52 including one circular central opening 54 and four slit-shaped openings 56 formed along the perimeter of the cover portion 50, which are arranged evenly spaced from one another. The fluid openings 52 are configured and arranged such that each of the fluid openings 52 directs a fluid stream 60 to a different direction to stimulate different areas of the rectal wall. As shown in FIG. 3, the fluid stream 60 exiting the center opening 54 is directed along an x-axis 66. Further, the slit-shaped peripheral openings 56, which are defined between the wall 64 of the flared-end portion 48 and the center portion 50, provide slanted fluid paths along the flared wall 64. Thus, each of the peripheral openings 56 directs the fluid stream 60 to a different direction around a polar coordinate.

In some situations, when the flow manifold is inserted and deployed in the rectum, some of the fluid streams 60 may be directed along the rectal axis, which do not provide rectal wall stimulations. The normal angle between the axis of the anal canal and the axis of the rectum is about 90 degrees. So, for example when a two opening design is used, it can be the case that one of the two openings is directed along the rectal axis. This will present a very low resistance to water exit from this opening. As a result, the water exit from the other opening, the one that is directed at the rectal wall, will have a lower water pressure than if both openings were directed at the rectal wall. This effect of reducing the pressure directed at the rectal wall because one opening is directed along the rectal axis will be proportionately less of a reduction, the larger the total number of openings. Also, a design that has at least three openings will ensure that stimulation is provided in at least two separate places, even if one of the three openings is directed along the rectal axis.

Preferably, the flow manifold 24 is a one-piece member, in which the flared member-end portion 48 and the cover portion 50 are continuously formed as a single-piece. Alternatively, the flow manifold can be formed as a two-piece device including a flared-end member and a cover member, in which the cover member is sealingly arranged in the flared-end member. Further, in some embodiments, the flow manifold 24 can include two, three, or four fluid openings, or more than five openings. Preferably, the flow manifold 24 has at least three fluid openings. Further, the fluid openings 52 can be arranged in various locations in the flow manifold 24, and can have different shapes. Once the hand pump 23 is actuated, the fluid flows into the flow lumen 58 of the flow manifold 24 and exits through the multiple openings 52.

The irrigation kit 10 can be configured to keep the stream pressure on the tissue at a safe, yet stimulatory level. This is done by adjusting the volume expelled by the hand pump 23 per squeeze, and the size of the openings 52.

In use, the reservoir 20 is filled with 350-400 cc of water, preferably at body temperature. The reservoir 20 is suspended by use of the opening 21 from, e.g. the left thumb. The patient sits on a toilet, and rests the left hand on the thigh, which also partially supports the reservoir 20. The irrigation kit 10 is held also by the left hand, perhaps by just holding the tubing portions 22, 28. The flow manifold 24 is then folded and inserted by the user into the rectum. Once the manifold is deployed in the rectum, the right hand will be free to hold and to operate the hand pump 23.

The hand pump 23 is designed with the one way valves 25, 26, which when squeezed allow irrigation fluid to pass through the flow lumen 58 and into the flow manifold 24. When the hand pump 23 is released, the fluid is drawn from the reservoir 20 into the pump body 40. The valves 25, 26 prevent back flow to the reservoir 20 and to the hand pump 23. The hand pump 23 is actuated, for example three times in quick succession, which will accomplish two things. First, about 160 cc of fluid will be instilled via the flow manifold 24 into the rectum. Second, the walls of the rectum near the rectal floor will be stimulated, in multiple separate places, by the water jets that are directed outward through the small slit-shaped openings 56 and the circular center opening 54 of the flow manifold 24. Because the openings 54, 56 are relatively small, and the pump action is relatively vigorous, a flow stream can be generated at a stimulatory pressure. The flow manifold 24, having more than two openings 52, generates fluid streams, which can stimulate multiple areas of the rectal wall, in a fashion that is similar to the traditional digital stimulation routine.

After the two pump instillation, the manifold 24 can be removed, and the bowel can be allowed to empty. This can then be followed by a repeat instillation, again inserting the manifold 24, pumping three times, and then allowing the bowel to empty.

All patents referred to herein, are incorporated herein in their entirety or by reference, whether or not specifically indicated as such within the text of this disclosure.

In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present device. It is to be understood that no limitation with respect to the specific embodiments illustrated is intended or should be inferred. The disclosure is intended to cover by the appended claims all such modifications as fall within the scope of the claims.

What is claimed is:

1. An anal irrigation kit, comprising:
    an irrigation liquid reservoir;
    a pump in fluid communication with the irrigation liquid reservoir; and
    a flow manifold in fluid communication with the pump, the flow manifold including multiple openings, wherein the flow manifold is made of a soft, resilient polymeric material, such that the flow manifold is sufficiently stiff to be pushed through an anal canal and self-deployable once in a rectum, but soft enough to be manually foldable for insertion into the rectum;
    the flow manifold further includes a distalmost flared-end portion including a flared wall with an outer surface area configured to sealingly engage the rectum as fluid flows through the flow manifold and a cover portion attached to a distalmost flared edge of the flared wall, wherein a flow lumen is defined by an enclosed inner surface area of the flared-end portion between the flared wall and the cover portion and a plurality of the multiple openings are arranged about the distalmost flared edge of the flared wall in fluid communication with the flow lumen wherein the irrigation liquid reservoir has an inlet, an inner wall and an outer wall, the inner wall and the outer wall being sealed together along peripheral edges to define a cavity; and the pump is a hand pump including a rigid outer wall, a top inlet and a bottom outlet; and the flow manifold has an entry end proximate the hand pump.

2. The anal irrigation kit of claim 1, wherein the flow manifold is made of a silicone rubber.

3. The anal irrigation kit of claim 1, wherein the distalmost flared edge of the flared wall is attached to the cover portion having a circular profile, the circular profile having a diameter between about 1.5 cm and about 7 cm.

4. The anal irrigation kit of claim 1, wherein the multiple openings are arranged on the cover portion, wherein the anal irrigation kit is configured to direct liquid streams in different directions through the multiple openings at a pressure sufficient to stimulate a rectal wall, wherein the multiple openings are configured such that at least one of the multiple openings directs the liquid stream toward the rectal wall at a pressure sufficient to trigger a reflex reaction.

5. The anal irrigation kit of claim 4, wherein the multiple openings include a center opening arranged proximate a center of the cover portion and at least three peripheral openings arranged along a periphery of the cover portion, wherein each of the peripheral openings directs a fluid stream toward a different location along a polar coordinate.

6. The anal irrigation kit of claim 1, wherein the irrigation liquid reservoir, the hand pump and the flow manifold are connected via a series of tubing portion.

7. The anal irrigation kit of claim 1, wherein at least one of the multiple openings is circumferentially located about the distalmost edge of the flared wall.

8. The anal irrigation kit of claim 1, wherein the hand pump has a first one-way valve located proximate the top inlet and a second one-way valve located proximate the bottom outlet.

9. The anal irrigation kit of claim 1, wherein the irrigation liquid reservoir includes a hole, wherein a circumference of the hole is of a distance to accommodate a user's thumb.

10. The anal irrigation kit of claim 1, further including a temperature indicator located on a wall of the irrigation liquid reservoir.

11. A handheld transanal irrigation kit having a proximal end and a distal end comprising:

an irrigation liquid reservoir, the irrigation liquid reservoir having an inlet, a first wall and a second wall, the first wall and the second wall are sealed together along peripheral edges to define a cavity;

a hand pump, the hand pump including a rigid outer wall, a top inlet and a bottom outlet, and having a first one-way valve located proximate the top inlet and having a second one-way valve located proximate the bottom outlet;

a resilient flow manifold, the flow manifold being constructed of a resilient material, the flow manifold having a flow lumen therethrough, the flow manifold having an entry end proximate the hand pump and a distalmost exit end, the distalmost exit end having a flared-end portion including a flared wall with an outer surface area configured to sealingly engage a rectum as fluid flows through the flow manifold and a cover portion attached to a distalmost flared edge of the flared wall, wherein a flow lumen is defined by an enclosed inner surface area of the flared-end portion between the flared wall and the cover portion and a plurality of openings are arranged about the distalmost flared edge of the flared wall in fluid communication with the flow lumen.

12. A method of emptying a bowel, comprising the steps of:

providing an anal irrigation kit including an irrigation liquid reservoir, a hand pump, and a soft flow manifold including multiple openings, the soft flow manifold further including a distalmost flared-end portion including a flared wall with an outer surface area configured to sealingly engage a rectum as fluid flows through the flow manifold and a cover portion attached to a distalmost flared edge of the flared wall, wherein a flow lumen is defined by an enclosed inner surface area of the flared-end portion between the flared wall and the cover portion and a plurality of the multiple openings are arranged about the distalmost flared edge of the flared wall in fluid communication with the flow lumen;

folding the soft flow manifold and inserting the folded soft flow manifold into the rectum; and instilling an irrigation liquid and stimulating a rectal wall simultaneously by operation of the hand pump.

13. The method of claim 12, wherein the soft flow manifold is formed of a resilient material, and configured to self-deploy once the folded soft flow manifold is in the rectum.

14. The method of claim 12, wherein the step of instilling an irrigation liquid and stimulating a rectal wall includes expelling liquid streams through the multiple openings, such that at least some of the liquid streams are directed to different areas of the rectal wall at a stimulatory pressure to trigger a defecatory response.

15. The method of claim 12, wherein the flared-end portion is folded to increase a bending stiffness of the flared-end portion for insertion into the rectum, wherein the flared-end portion self-deploys in the rectum without a user intervention to provide for hands-free retention of the flow manifold in the rectum during the step of instilling an irrigation liquid.

16. The method of claim 12, wherein the method empties the bowel by mobilizing bowel contents in the irrigation liquid and simultaneously stimulating a defecatory response by expelling irrigation liquid streams at multiple locations along the rectal wall at a stimulatory pressure.

* * * * *

UNITED STATES PATENT AND TRADEMARK OFFICE
CERTIFICATE OF CORRECTION

PATENT NO. : 9,770,548 B2
APPLICATION NO. : 14/354027
DATED : September 26, 2017
INVENTOR(S) : Thomas H. Gilman It is certified that error appears in the above-identified patent and that said Letters Patent is hereby corrected as shown below:

In the Specification

Column 2, Line 4, delete "rum" and insert --turn--.

Column 5, Line 18, delete "now" and insert --flow--.

Column 5, Line 67, delete "exiting," and insert --exiting--.

Column 7, Line 8, delete "was" and insert --ways--.

Signed and Sealed this
Fourteenth Day of November, 2017

Joseph Matal
*Performing the Functions and Duties of the*
*Under Secretary of Commerce for Intellectual Property and*
*Director of the United States Patent and Trademark Office*